United States Patent
Engelbreth et al.

(10) Patent No.: US 10,960,153 B2
(45) Date of Patent: Mar. 30, 2021

(54) DELIVERY DEVICE AND KIT, AND METHOD OF USE

(71) Applicant: TRUDELL MEDICAL INTERNATIONAL, London (CA)

(72) Inventors: Daniel Engelbreth, London (CA); Martin P. Foley, London (CA); Jerry Grychowski, Batavia, IL (US); James Schmidt, London (CA); Jennifer Pevler, London (CA)

(73) Assignee: Trudell Medical International, London (CA)

( * ) Notice: Subject to any disclaimer, the term of this patent is extended or adjusted under 35 U.S.C. 154(b) by 849 days.

(21) Appl. No.: 15/447,537

(22) Filed: Mar. 2, 2017

(65) Prior Publication Data

US 2017/0173281 A1    Jun. 22, 2017

Related U.S. Application Data

(63) Continuation of application No. 14/213,275, filed on Mar. 14, 2014, now Pat. No. 9,700,688.

(Continued)

(51) Int. Cl.
   *A61M 15/00* (2006.01)
   *A61J 17/00* (2006.01)
   *A61J 11/00* (2006.01)
   *A61M 16/06* (2006.01)
   *A61J 7/00* (2006.01)

(52) U.S. Cl.
   CPC .......... *A61M 15/0086* (2013.01); *A61J 11/00* (2013.01); *A61J 17/001* (2015.05); *A61M 15/009* (2013.01); *A61M 15/0016* (2014.02); *A61M 15/0018* (2014.02); *A61M 15/0068* (2014.02); *A61M 16/06* (2013.01);
   (Continued)

(58) Field of Classification Search
   CPC ............ A61M 15/0086; A61M 15/009; A61M 15/0016; A61M 15/0018; A61M 15/0068; A61M 2210/0618; A61M 2240/00; A61J 17/006; A61J 7/0053; A61J 17/001; A61J 11/00
   See application file for complete search history.

(56) References Cited

U.S. PATENT DOCUMENTS 3,861,210 A    1/1975   Griverus
4,253,468 A    3/1981   Lehmbeck
(Continued)

FOREIGN PATENT DOCUMENTS

WO    WO 2011125061 A2    10/2011
WO    WO 2011137905 A1    11/2011
WO    WO 2012173992 A1    12/2012

OTHER PUBLICATIONS

Display poster board, Newhouse et al., Prototype InspiraChamber™ and SmootherMask®—A Unique System with Optimized Particle Size Selectivity and Minimal Dead Space, 5 pages (various enlarged views).

*Primary Examiner* — Steven O Douglas
(74) *Attorney, Agent, or Firm* — Brinks Gilson & Lione

(57) ABSTRACT

A nasal mask has a flexible bottom edge portion and side portions. A delivery device includes a holding chamber coupled to the nasal mask. A method of delivering an inhalable substance includes positioning a nose of a user in a cavity of the nasal mask, inhaling through the nose, and orally soothing the user with a soothing device.

23 Claims, 11 Drawing Sheets

Related U.S. Application Data

(60) Provisional application No. 61/792,583, filed on Mar. 15, 2013.

(52) U.S. Cl.
CPC ..... *A61J 7/0053* (2013.01); *A61M 2210/0618* (2013.01); *A61M 2240/00* (2013.01)

(56) References Cited

U.S. PATENT DOCUMENTS

| | | | |
|---|---|---|---|
| 5,427,089 A * | 6/1995 | Kraemer | A61M 15/0086 128/200.14 |
| 5,592,935 A | 1/1997 | Elstran et al. | |
| 5,598,835 A | 2/1997 | Von Schrader | |
| 5,685,291 A | 11/1997 | Marsh | |
| 5,848,587 A | 12/1998 | King | |
| 5,904,140 A | 5/1999 | McGoogan | |
| 5,988,160 A | 11/1999 | Foley et al. | |
| 6,012,455 A | 1/2000 | Goldstein | |
| 6,014,972 A | 1/2000 | Sladek | |
| 6,336,453 B1 | 1/2002 | Scarrott et al. | |
| 6,394,085 B1 | 5/2002 | Hardy et al. | |
| 6,412,481 B1 | 7/2002 | Bienvenu et al. | |
| 6,412,488 B1 * | 7/2002 | Barnett | A61M 16/06 128/205.25 |
| 6,470,882 B1 | 10/2002 | Newhouse et al. | |
| 6,557,548 B1 | 5/2003 | Dickson | |
| 6,578,571 B1 | 6/2003 | Watt | |
| 6,615,824 B2 | 9/2003 | Power | |
| 6,626,168 B1 | 9/2003 | Carroll et al. | |
| 6,725,858 B2 | 4/2004 | Loescher | |
| 6,789,543 B2 | 9/2004 | Cannon | |
| 6,904,908 B2 | 6/2005 | Bruce et al. | |
| 7,204,245 B2 | 4/2007 | Johnson et al. | |
| 7,318,433 B2 | 1/2008 | Cockerham | |
| 7,360,537 B2 | 4/2008 | Snyder et al. | |
| 7,905,228 B2 | 3/2011 | Blacker et al. | |
| 8,122,881 B2 * | 2/2012 | Giroux | A61M 11/00 128/203.12 |
| 8,151,794 B2 | 4/2012 | Meyer et al. | |
| 8,225,785 B2 | 7/2012 | Richards et al. | |
| D754,845 S | 4/2016 | Duran | |
| 9,700,688 B2 * | 7/2017 | Engelbreth | A61M 15/0086 |
| 2002/0112724 A1 | 8/2002 | Newhouse et al. | |
| 2005/0039746 A1 | 2/2005 | Grychowski et al. | |
| 2006/0254479 A1 | 11/2006 | Luchetti et al. | |
| 2007/0000495 A1 | 1/2007 | Matula, Jr. et al. | |
| 2010/0000525 A1 * | 1/2010 | Lee | A61M 16/0666 128/202.13 |
| 2010/0101570 A1 | 4/2010 | Meyer et al. | |
| 2010/0147298 A1 | 6/2010 | Loescher et al. | |
| 2012/0285236 A1 | 11/2012 | Haartsen et al. | |
| 2012/0291779 A1 | 11/2012 | Haartsen et al. | |
| 2012/0318261 A1 | 12/2012 | Newhouse et al. | |
| 2012/0318265 A1 | 12/2012 | Amirav et al. | |
| 2013/0008436 A1 | 1/2013 | Von Hollen et al. | |
| 2013/0025594 A1 | 1/2013 | Wachtel et al. | |
| 2013/0118485 A1 * | 5/2013 | Shahaf | A61J 7/0053 128/202.15 |
| 2017/0173281 A1 | 6/2017 | Engelbreth et al. | |

* cited by examiner

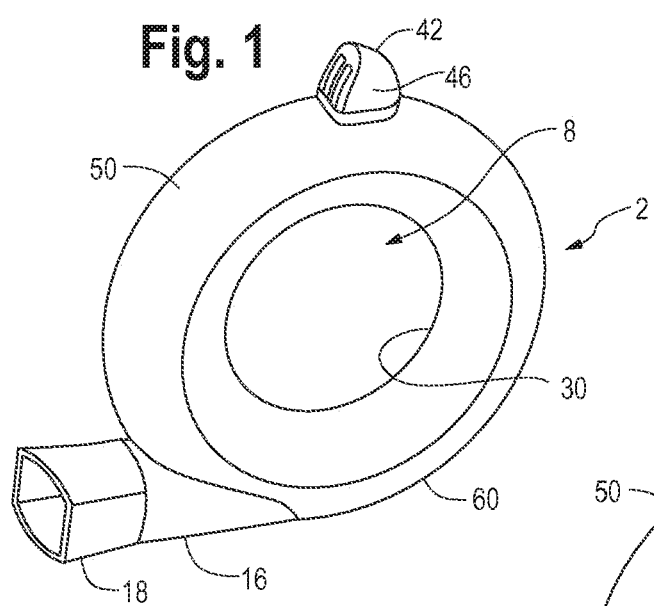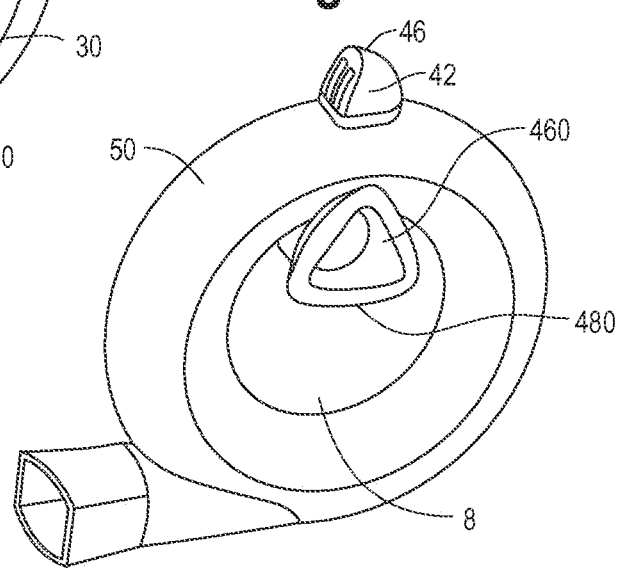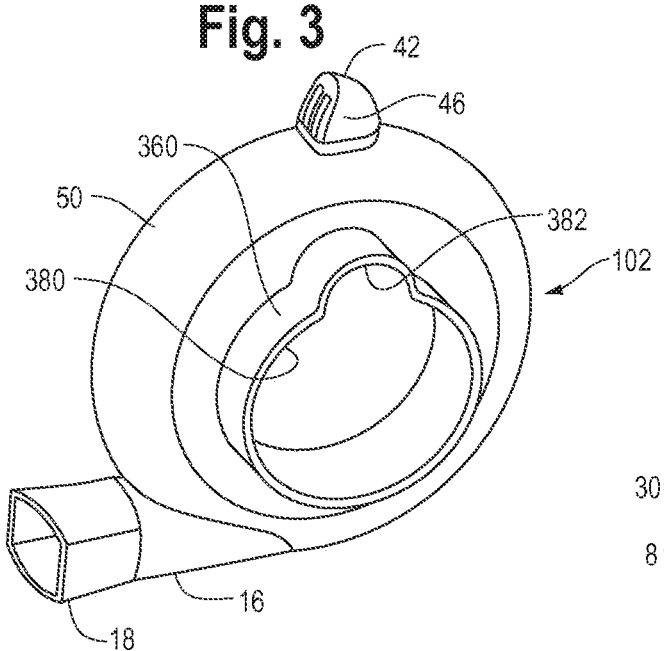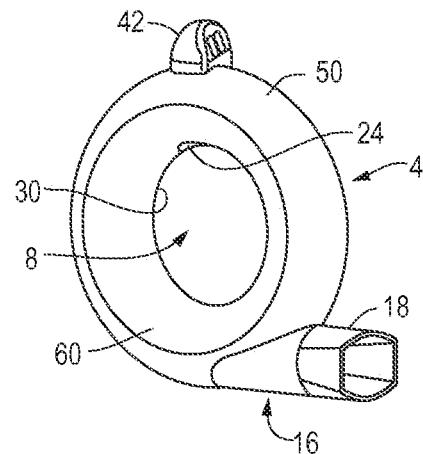

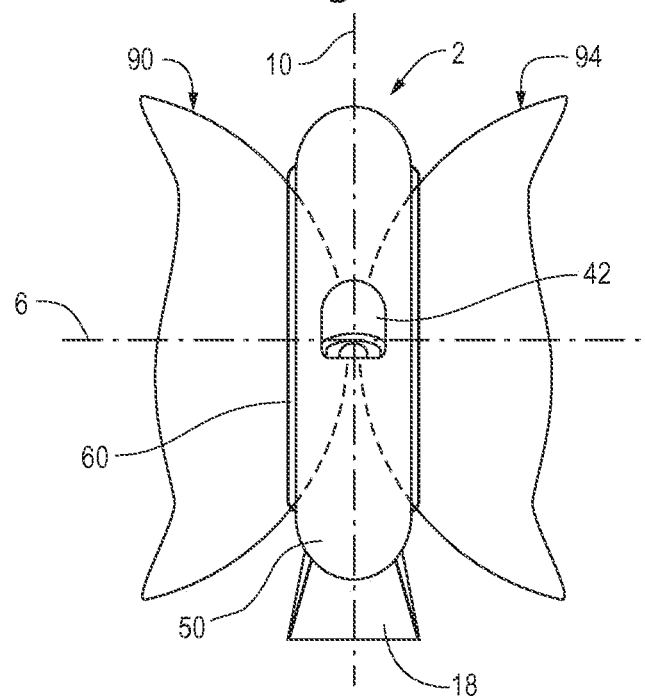
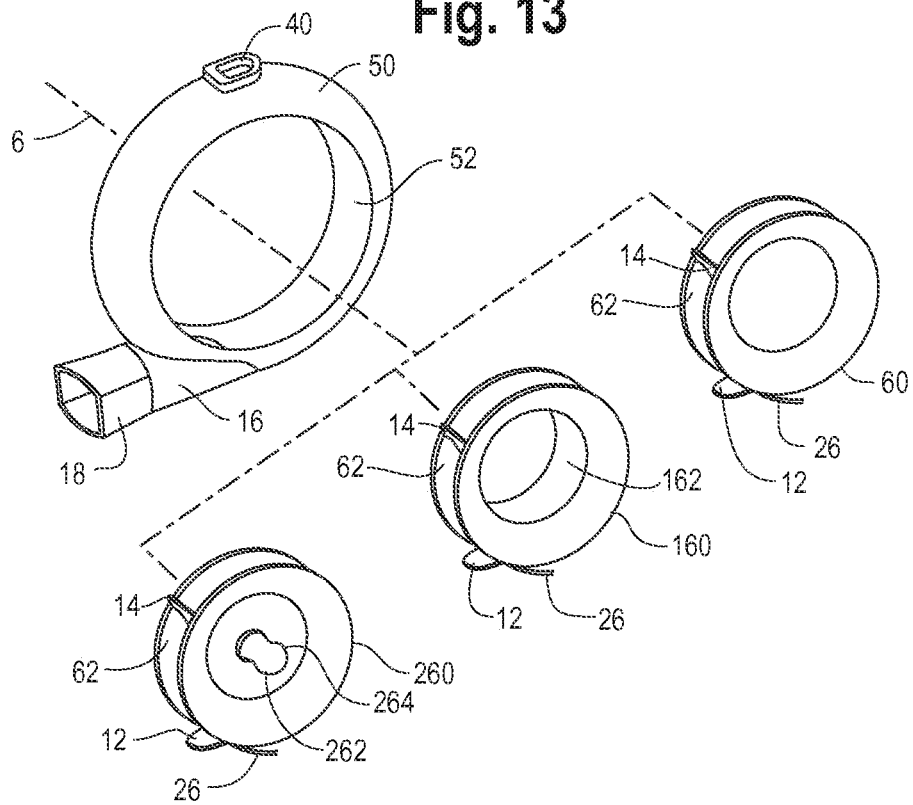

US 10,960,153 B2

DELIVERY DEVICE AND KIT, AND METHOD OF USE

This application is a continuation of U.S. application Ser. No. 14/213,275, filed Mar. 14, 2014, which application claims the benefit of U.S. Provisional Application No. 61/792,583, filed Mar. 15, 2013, the entire disclosures of which are hereby incorporated herein by reference.

TECHNICAL FIELD

The present invention relates generally to a delivery device, including an aerosol delivery device suitable for delivering an aerosolized substance, such as a medicament, to the nasal cavities of an infant while being soothed orally, and also to aerosol delivery kits and methods of delivering aerosol medicament or the like.

BACKGROUND

It is well known to deliver aerosolized medicaments to a patient via various devices, including nebulizers and aerosol dispensing devices, such as pressurized Metered Dose Inhalers (PMDI's), in order to treat various conditions and diseases, including but not limited to various respiratory conditions and diseases such as asthma. It is also desirable to deliver certain gases, such as oxygen, or vapor of a substance, such an aromatic substance, to a patient having difficulty breathing. In some configurations, the device is configured with a patient interface mouthpiece, which is inserted into the mouth of a user such that the aerosolized medicament can be inhaled into the lungs of the user. In other embodiments, the patient interface is configured as a mask, which typically is fitted around the nose and mouth of the user so as to maximize and ensure inhalation of the aerosolized medicament into the lungs of the user.

These types of patient interfaces may not be ideally suited for certain patients, however, such as infants. Infants tend to reject having a mask positioned over their face and thereby covering their nose and mouth. The infant may become cranky, irritable and prone to crying, which reduces the likelihood of delivering a proper amount of the desired substance, such as a medicament.

In addition, infants up to the age of 18 months are primarily nose breathers. With such patients, the mouth rarely has a role in inhalation except in situations where there is a complete occlusion of the nasal passageways. Moreover, infants are not capable of understanding and/or following instructions to inhale only through their mouth, e.g., if a mouthpiece is introduced therein, and the likelihood of delivering the proper amount of medicament is greatly reduced with such a device. As such, a need remains for an improved device capable of delivering an aerosolized medicament, gas, or other desired substance to the nasal passageways of a patient, particularly infants, without causing anxiety and distress to the patient.

SUMMARY

Briefly stated, in one aspect, one embodiment of a delivery device includes a toroidal shaped housing defining an interior chamber and a central open space. The housing includes an input port communicating with the interior chamber and a delivery port positioned on an inner periphery of the housing. The delivery port is in fluid communication between the interior chamber and the central open space. The delivery port is spaced from the input port, which is adapted to receive an aerosolized medicament.

In another aspect, one embodiment of a delivery device kit includes an outer ring-like housing component defining at least in part a holding chamber and having an input port communicating with the holding chamber. A first inner ring-like housing component defines at least in part a first holding chamber and a first central through opening shaped to matingly receive at least a portion of a breast. The first inner ring-like housing component includes a first delivery port. The first inner ring-like housing component and the outer ring-like component are configured for mateable coupling to define a first enclosed holding chamber. A second inner ring-like housing component defines at least in part a second holding chamber and a central open space. The second inner ring-like housing component includes a second delivery port. The second inner ring-like housing component and the outer ring-like component are configured for mateable coupling to define a second enclosed holding chamber. The second inner ring-like housing includes a soother device extending into the central open space. A third inner ring-like housing component defines at least in part a third holding chamber and a second central through opening. The third inner ring-like housing component includes a third delivery port. The third inner ring-like housing component and the outer ring-like component are configured for mateable coupling to define a third enclosed holding chamber. The third inner ring-like housing has an annular wall defining the second central through opening. The annular wall is shaped to matingly receive and seal against a bottle extending into the second central through opening.

In another embodiment, a delivery device kit includes an outer ring-like housing component defining at least in part a first cavity and having an input port communicating with the first cavity. A plurality of inner ring-like housing components each define at least in part a second cavity, a central space, and a delivery port, wherein each of the inner ring-like housing components is configured to individually mate with the outer ring-like component such that the first and second cavities define an enclosed holding chamber. Each of the inner ring-like housing components includes a user side and a provider side, wherein at least one of the user side or provider side of each of the plurality of inner ring-like housing components is configured differently from the user side or provider side of others of the plurality of inner ring-like housing components.

In another aspect, one embodiment of a method of delivering an aerosolized medicament includes positioning a nose and a mouth of a user in a central opening defined by a ring-like housing, introducing an aerosolized medicament through an input port into an interior chamber defined by the ring-like housing and inhaling through the nose and thereby drawing the aerosolized medicament from the interior chamber into the central opening through a delivery port disposed on an inner periphery of the ring-like housing. The method further includes exhaling through the nose into the central opening and soothing the user by positioning a soothing device located in the central opening in the mouth of the user during said inhaling and exhaling. The soothing device, for example, may be one of a nipple extending from a breast, a bottle or a pacifier.

The various aspects and embodiments provide significant advantages over other delivery devices, kits and methods. Typically, an infant will remain calm, and continue with a regular and uninterrupted breathing cycle, when being soothed orally, for example by nursing, feeding from a bottle or sucking on a pacifier. As such, breathing is not compromised when the infant is nursing, feeding or sucking on a pacifier. The present embodiments facilitate the administration to an infant of an aerosolized medicament from a nebulizer, pressurized metered dose inhaler ("pMDI") or other aerosol dispensing device. The embodiments allow a caregiver to deliver an aerosolized medicament to the nasal passageways of the user while allowing and providing for the user to nurse, feed, suck or otherwise be soothed during the delivery sequence. In addition, the modular construction of the device, with a plurality of different patient soother interfaces provides the caregiver with a variety of choices to administer the medications. For example, in various public venues, or in other situations where nursing and/or feeding may not be convenient or practical, including hospital settings, the caregiver may use the pacifier soother interface to sooth the infant while delivering the medicament. The embodiments also can facilitate the delivery of gases, such as oxygen, or a desired substance in vapor form to the user for inhalation.

The present embodiments of the invention, together with further objects and advantages, will be best understood by reference to the following detailed description taken in conjunction with the accompanying drawings.

BRIEF DESCRIPTION OF THE DRAWINGS

FIG. 1 is a perspective view of one embodiment of a delivery device.

FIG. 2 is a perspective view of an alternative embodiment of a delivery device.

FIG. 3 is a perspective view of another alternative embodiment of a delivery device.

FIG. 4 is an opposite side perspective view of the embodiment of a delivery device shown in FIG. 1.

FIG. 12 is a top, schematic side view of an infant nursing while using the delivery device shown in FIG. 4.

FIG. 13 is a perspective view of a delivery device kit having a plurality of patient soothing interfaces.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" ring-like housing components may refer to any sequence of such members, and is not limited to the first and second ring-like housing components of a particular configuration unless otherwise specified. It should be understood that the terms "input port" and "delivery port" refer to the function of the ports during an inhalation phase, and that the delivery port may serve the opposite function (removal or exit) during an exhalation phase. It should be understood that the term "infant" as used herein refers to neonatal or pediatric patients and also includes children for whom a pacifier is comforting and useful for delivering aerosolized medication, gases or other therapeutic substance for inhalation.

Referring to FIGS. 1-3, 14 and 15, various embodiments of a delivery device are shown. In each of the embodiments, the delivery device includes a housing 2, 102, 202, 302, 402 defining an interior chamber 4. In one embodiment, the housing has a "toroidal" shape, defined as a surface generated by a geometric shape rotating about, but not intersecting or containing, an axis 6 in its own plane, or as a ring-like structure. For example and without limitation, the housing 2, 102, 202, 302, 402 may be substantially donut shaped, with a hollow interior, such as when the geometric shape, taken in cross section is a circle. In other embodiments, the cross-sectional shape may be an ellipse, a polygon, or a combination of curved and linear portions, whether closed or open. In addition, in some embodiments, the geometric shape may be rotated at constant radius "r" about the axis 6, e.g., thereby forming the donut shape with a circular central open space 8 or center opening, while in other embodiments the distance between the axis and the inner periphery may vary, for example by having an elliptically shaped central open space or opening, or defining some other shape such as an oval, obround, etc.

Figure 5:
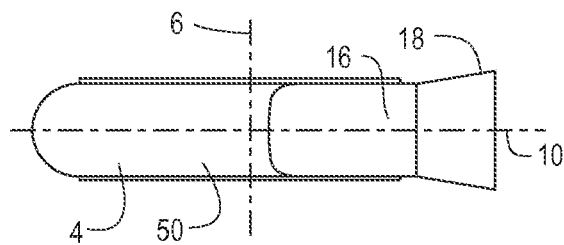
FIG. 5 is a top view of the delivery device shown in FIG. 4.
Figure 6:
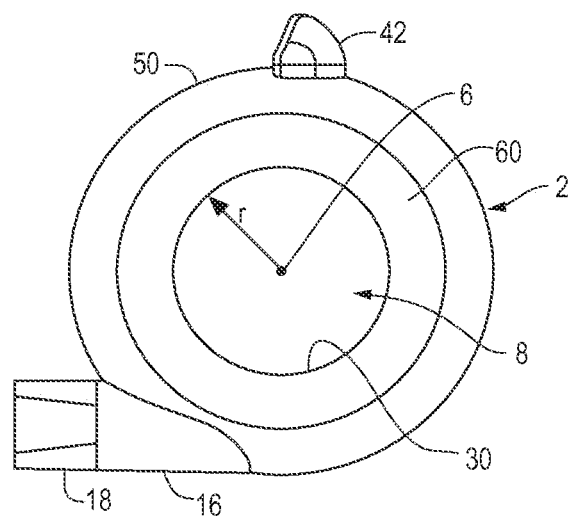
FIG. 6 is a first side view of the delivery device shown in FIG. 4.
Figure 7:
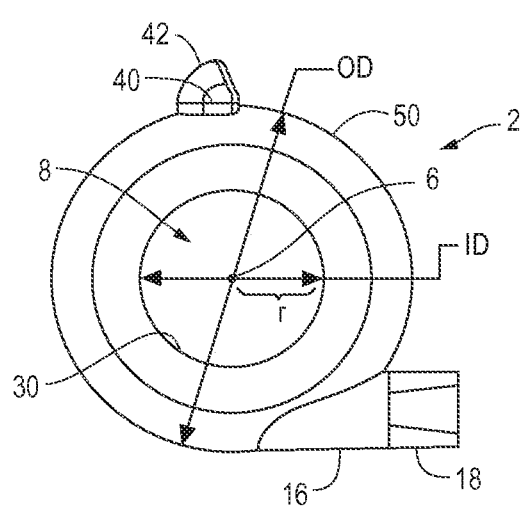
FIG. 7 is a second side view of the delivery device shown in FIG. 4.
Figure 8:
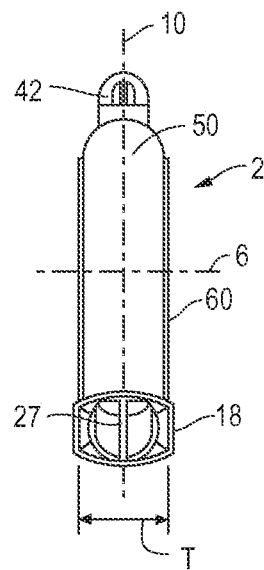
FIG. 8 is a front view of the delivery device shown in FIG. 4.

In the various embodiments shown, the housing is planar, and is centered on a plane 10 lying substantially perpendicular to the axis 6 defining the toroidal shape. In other embodiments, the housing may be non-planar. Referring to FIG. 8, the housing may be configured with various thicknesses (T) in the axial direction, for example from about 20 mm to about 60 mm, and in one embodiment from about 26 mm to about 50 mm. In this way, differently sized devices, e.g., small, medium and large, may be provided depending on the size and shape of the provider's breasts and size and shape of the head and/or face of the user. In the embodiments shown, the housing forms and defines the central open space 8, or central opening. In one embodiment as shown in FIGS. 6 and 7, wherein the central open space is circular, the inner diameter (ID) is from about 52 mm to about 75 mm. Again, differently sized openings may be provided depending on the size and shape of the provider's breasts and size and shape of the head and/or face of the user. Also in one embodiment, wherein the housing 4 is formed about the axis 6 at a constant radius "r", the outer diameter (OD) of the housing is from about 104 mm to about 130 mm.

Figure 9:
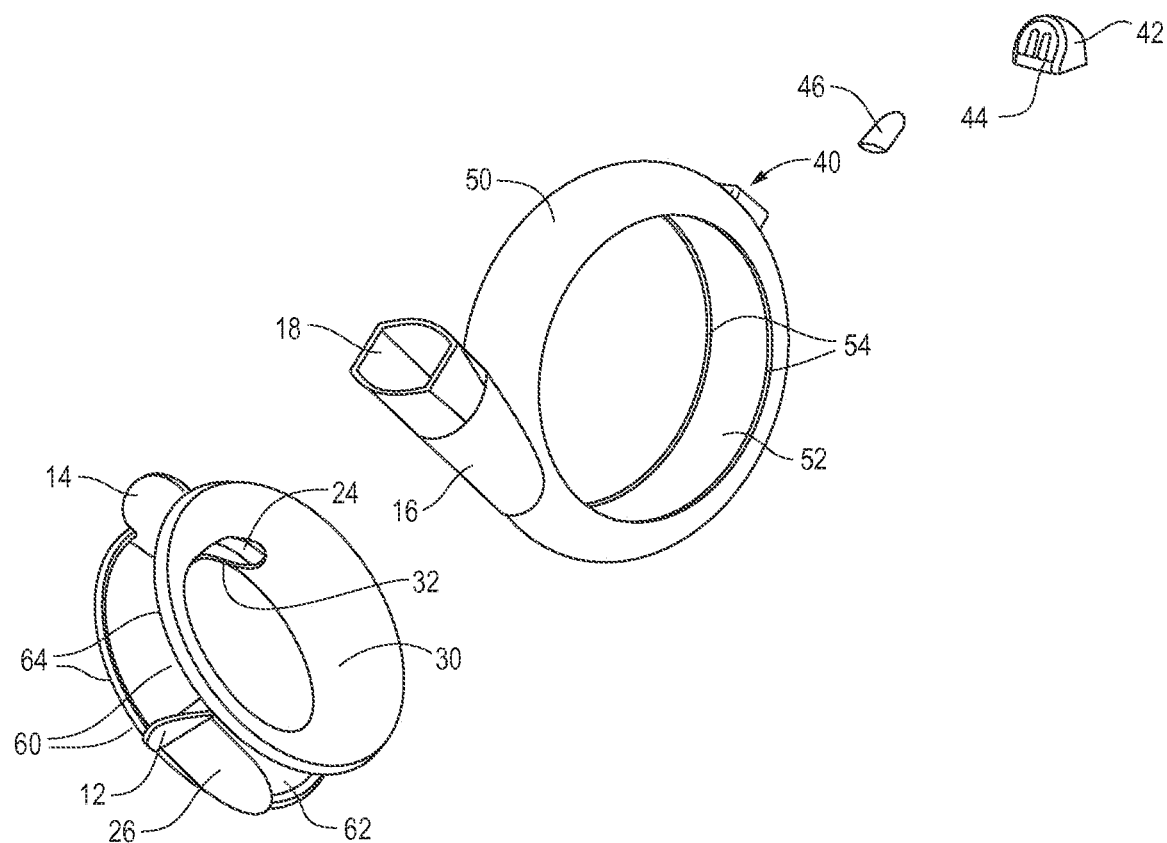
FIG. 9 is an exploded perspective view of the delivery device shown in FIG. 4.
Figure 10:
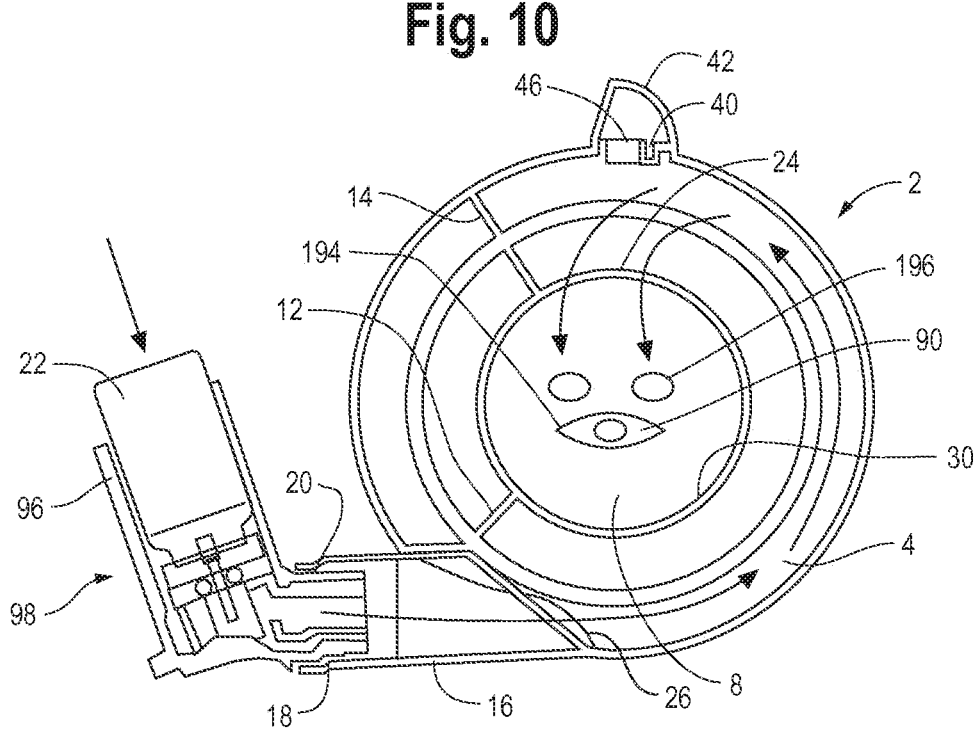
FIG. 10 is a schematic side view of the delivery device shown in FIG. 4 during an inhalation sequence.
Figure 11:
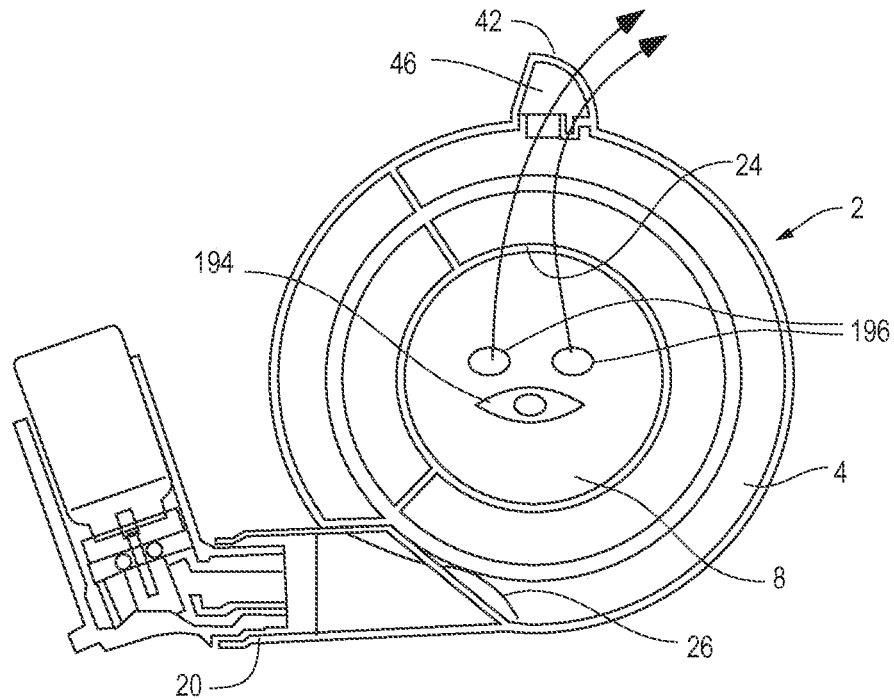
FIG. 11 is a schematic side view of the delivery device shown in FIG. 4 during an exhalation sequence.

The interior chamber 4 may be formed around the entirety of the housing, or around only a portion thereof as shown for example in FIGS. 9-11, wherein a pair of walls 12, 14 close off a portion of the housing interior and define the interior chamber, thereby creating a flow path within the interior chamber. An input port 16 extends from the housing and is configured and shaped to receive a source of aerosolized medicament, for example a container 22 of medicament. For example, in one embodiment the input port includes a MDI boot portal 18, which is dimensioned and shaped to receive a mouthpiece portion 20 of an MDI actuator boot 96 as shown in FIGS. 10 and 11. The boot portal 18 may also be sized and shaped to receive a mouthpiece or output end of a valved holding chamber (VHC), spacer, nebulizer or other known aerosol delivery devices. The input port 16 may also be configured to receive tubing or other similar conduit suited to deliver oxygen or other gases or a vapor from a vapor emitter. The boot portal 18 may be made of a flexible material such as TPE or silicone, thereby allowing it to conform to and seal with differently shaped MDI, VHC, spacer or nebulizer output ends, such as mouthpieces 20.

In one embodiment, a one-way inhalation valve 26 is positioned adjacent to and covering an interior passageway of the input port 16, which is in fluid communication with the interior chamber 4. The one-way inhalation valve 26 may be configured as a flap valve, duckbill valve, center pin valve, or other known types of valves so as to allow a one-way flow of aerosolized medicament from a MDI container 22, VHC or other delivery device to the interior chamber 4. The input port 16 may have a grid 27 or valve seat disposed across the opening to prohibit access to the valve, while providing a surface for the valve, e.g., a flap valve, to seat against during an exhalation sequence.

At a second location spaced from the input port, a delivery port 24 is positioned on an inner periphery 30 of the housing 4 and is in fluid communication between the interior chamber 4 and the central open space 8. In various embodiments, a two-way valve may be positioned over the delivery port. The delivery port 24 may be formed as an opening in a wall of the housing 4, and may include one or more bars 32 or a grid-like structure to prevent the incursion of foreign bodies into or out of the delivery port. In some embodiments, a filter may be positioned over the delivery port.

At a third location, an exhalation port 40 is in fluid communication between the interior chamber 4 and the ambient environment outside of the central open space. For example, in one embodiment, the exhalation port 40 is positioned on an outer periphery 50 of the housing. A one-way exhalation valve 46, configured in various embodiments as a flap valve, duckbill valve, center pin valve, etc., is positioned adjacent the exhalation port 40 and permits a one-way fluid communication from the interior chamber 4 to the ambient environment. A shroud 42, shown as a curved clam-shell housing, surrounds and protects the valve. In one embodiment, the valve 46 is secured or trapped between the shroud 42 and housing 4, while in another embodiment, the valve 46 is coupled to the shroud, which in turn is connected to the housing, for example by a snap fit, etc.. A bar or grid 44 may be formed across the opening of the shroud 42 to prevent access to the valve 46, and to provide a valve seat for the valve 46 to seat against during the exhalation sequence. The shroud may be made of a clear material such that the exhalation valve 46 is visible to a caregiver, which may monitor the position and movement of the exhalation valve 46 to determine and ensure the user is exhaling. In one embodiment, an indicator is used which provides a visual indication of when the infant is inhaling. The operation, construction and use of this type of inhalation visual indicator is further disclosed in U.S. Pat. No. 7,201,165, the entire disclosure of which is hereby incorporated herein by reference.

In various embodiments, the housing 4 is configured with an outer ring-like housing component 50 and an inner ring-like housing component 60, 160, 260, 360, 460. The outer ring-like housing component 50 forms and defines the input port 16 and exhalation port 40, while the inner ring-like housing components 60, 160, 260, 360, 460 each form and define the delivery port 24, the walls 12, 14 and the inhalation valve 26, all of which are integrally formed in one embodiment as shown in FIG. 9. In one embodiment, the outer ring-like housing component 50 is made of a relatively rigid material, such as a polymer based material or metal. The polymer based material may be made of or coated with various anti-static materials. In one embodiment, the outer ring-like housing component is made from an anti-static material, as disclosed for example and without limitation in U.S. Pat. No. 7,360,537, which is hereby incorporated herein by reference in its entirety. In one embodiment, the antistatic material, or coating applied to the housing, has a surface resistivity of less than about 10E12 ohm/sq., and preferably between about 10E10 and about 10E12 ohm/sq. Further examples of housings used in MDI ventilator assemblies are disclosed in U.S. Publication No. US 2005-39746A1 (entitled Ventilator Circuit and Method for the User Thereof), and U.S. Publication No. US 2006-0254479A1 (entitled Ventilator Circuit and Method for the User Thereof), the entire disclosures of which are hereby incorporated herein by reference.

Figure 17:
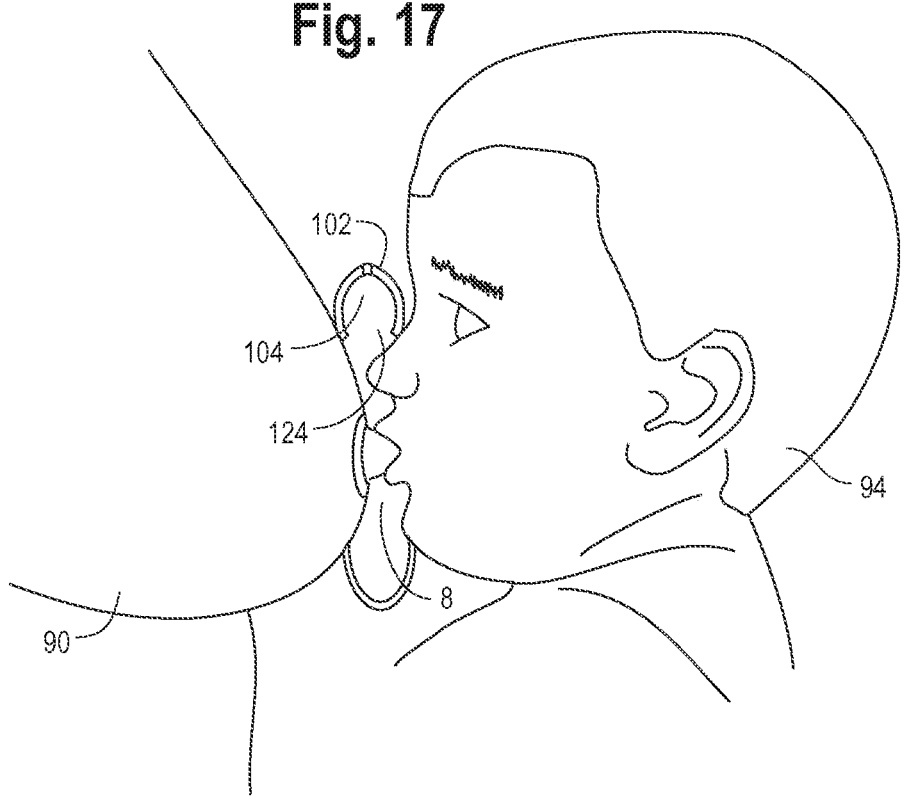
FIG. 17 is a side cross-sectional view of a user and a provider with an alternative embodiment of a delivery device disposed therebetween.
Figure 18:
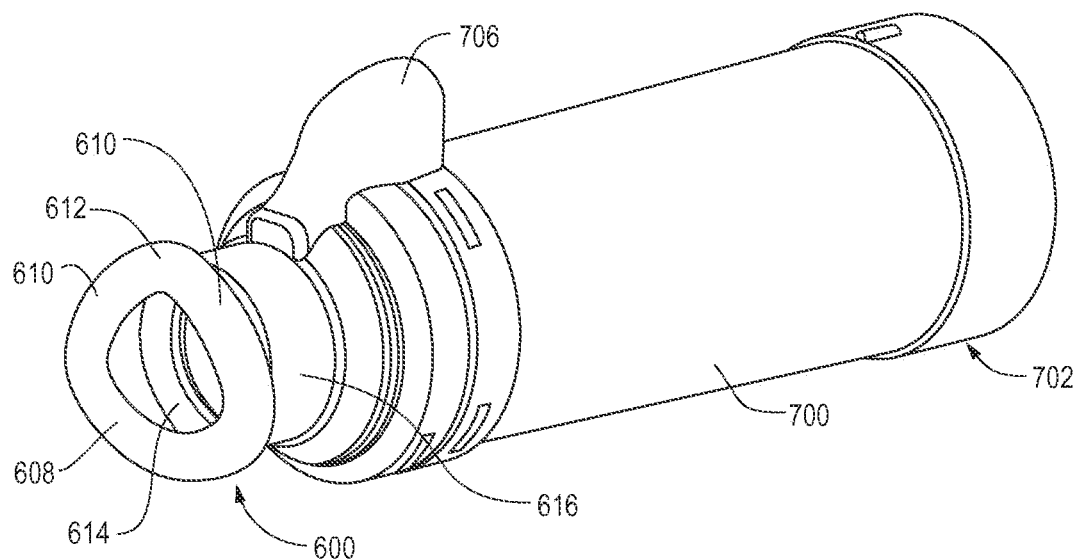
FIG. 18 is a perspective view of an alternative embodiment of a deliver device.
Figure 19:
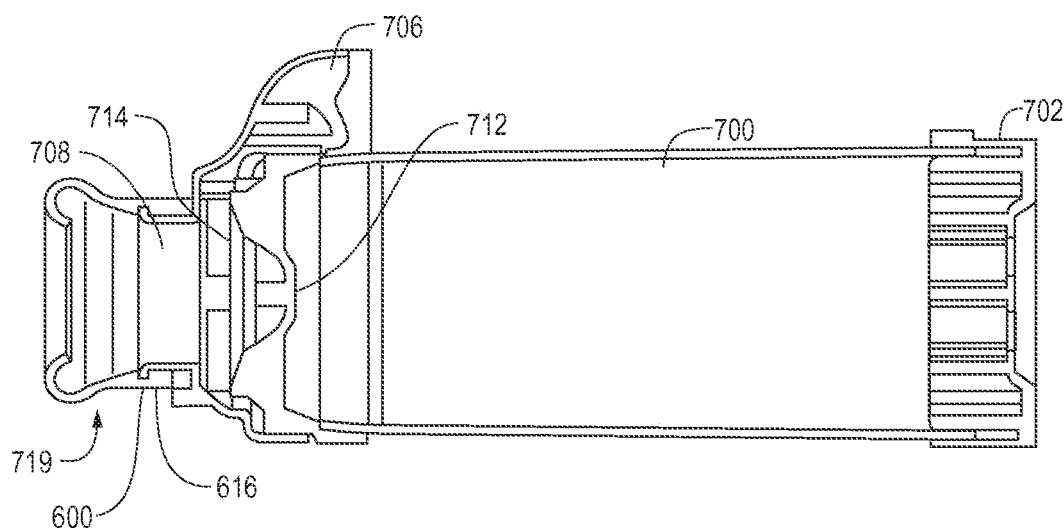
FIG. 19 is a cross-sectional view of the delivery device shown in FIG. 18.
Figure 20A:
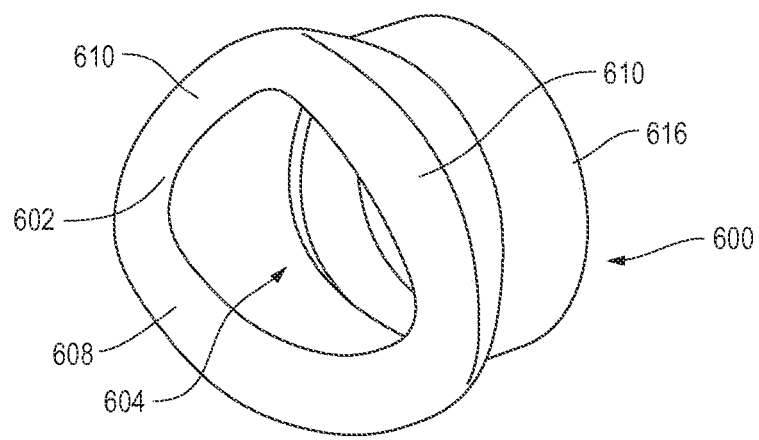
FIGS. 20A-C show one embodiment of a nasal mask in perspective view, front view and cross-sectional view respectively.
Figure 20B:
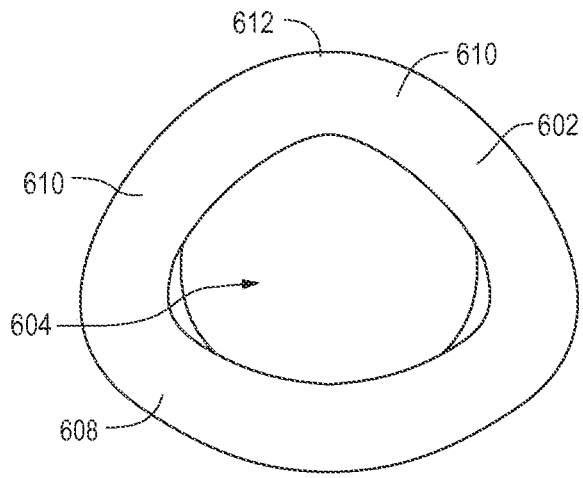
Figure 20C:
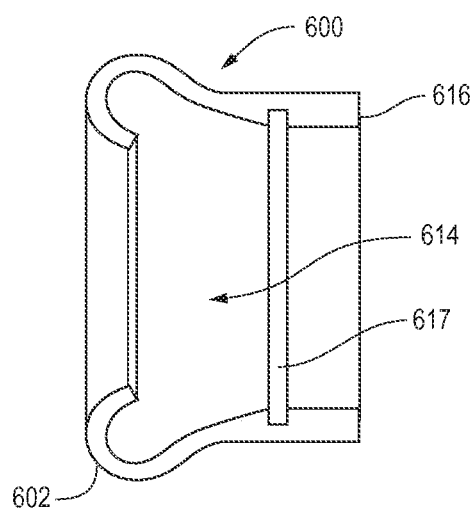
Figure 21:
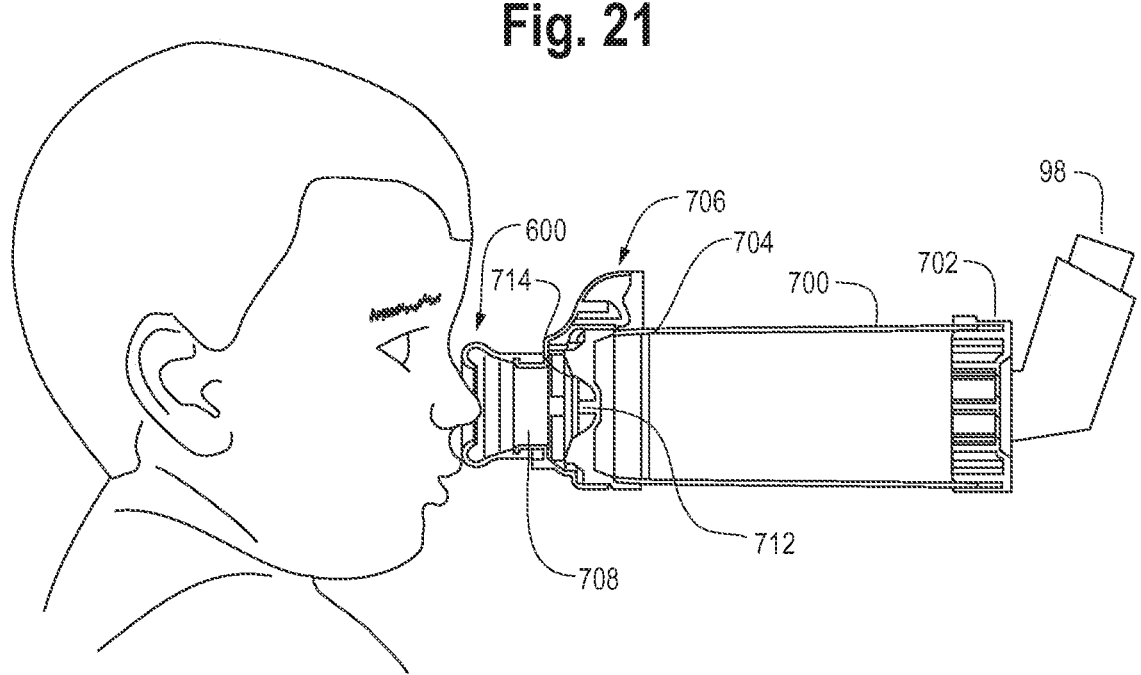
FIG. 21 is a side view of the delivery device shown in FIG. 18 when in use with a patient.

It should be understood that the housing may be integrally molded as a single ring-like housing component, for example made of silicone. In addition, as shown in FIG. 17, the inner peripheral wall of the housing may be left open, such that the cross-section of the entire housing 102 is C-shaped, with a provider side of the housing sealing again the provider and the use side sealing agains the face of the user, and with the interior chamber 104 opening along the inner periphery into the central opening 8. In this way, the mouth 124 of the C-shaped housing 102 defines the delivery portal. Notwithstanding that the cross-sectional shape is not a closed geometric shape, this embodiment is still considered to have a "toroidal" shape. In essence, the inner ring-like housing component may be omitted with an inhalation valve secured to the housing.

The inner ring-like housing component 60, 160, 260, 360, 460 is made of a relatively flexible, soft and resilient material, such as silicone, so as to provide a comfortable interface that more easily seals with the user's face on a user side of the device, and a caregiver's breast or bottle on an opposite provider side of the device. The outer ring-like housing component 50 and the inner ring-like housing component 60, 160, 260, 360, 460 each define in part a partial interior cavity 52, 62, or portion the interior chamber 4, and when joined, in combination define the interior chamber 4, which may function as a holding chamber, as shown in FIG. 9. The outer and inner ring-like housings 50, 60, 160, 260, 360, 460 may be joined by inner edges 54 of the outer ring-like housing interfacing with and fitting in annular grooves 64 formed in outer edges 66 of the inner ring-like housing. In other embodiments, the grooves may be formed on the outer ring-like housing, with the edges of the inner ring-like component interfacing therewith.

Referring to FIGS. 1-3 and 13-15, the inner ring-like housing component 60, 160, 260, 360, 460 may be configured in different ways. Indeed, in one embodiment a delivery device kit may be configured as a modular system, including for example an outer ring-like housing 40, and a plurality of differently configured inner ring-like housings 60, 160, 260, 360, 460. For example, as shown in FIGS. 1, 12 and 13, the inner ring-like housing component 60 may be symmetrical relative to the plane 10, with each side of the ring-like component having a curved shape in cross-section, whether concave or convex and with the central open space 8 configured as a through opening. In other embodiments, shown for example in FIGS. 2, 3, 14 and 15, the inner ring-like housing component 160, 260, 360, 460 is non-symmetrical. For example, as shown in the embodiment of FIG. 2, the inner ring-like housing component 460 includes a nasal mask 480 is positioned in the central opening 8 and in fluid communication with the delivery port. The mask 480 is positioned adjacent the inner periphery 30 so as to maintain the central space as a through opening to allow access by a user 94 to a soother device such as breast 90 or bottle 164.

As shown in FIG. 3, one side of the inner ring-like housing component 360 may be configured with an annular gasket 380 or mask extending substantially parallel to the axis from a "user" side of the housing. The mask may be configured with an irregular, non-circular shape, for example with a recess 380 shaped to fit over the outside of the user's nose. The gasket or wall seals with the user's face.

Figure 15:
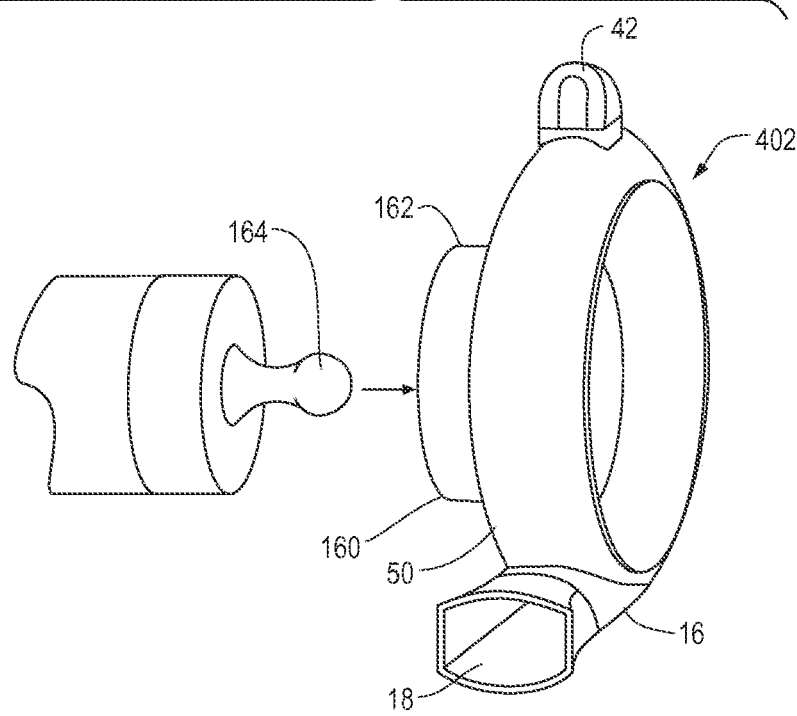
FIG. 15 is a perspective view of another alternative embodiment of a delivery device.
Figure 16:
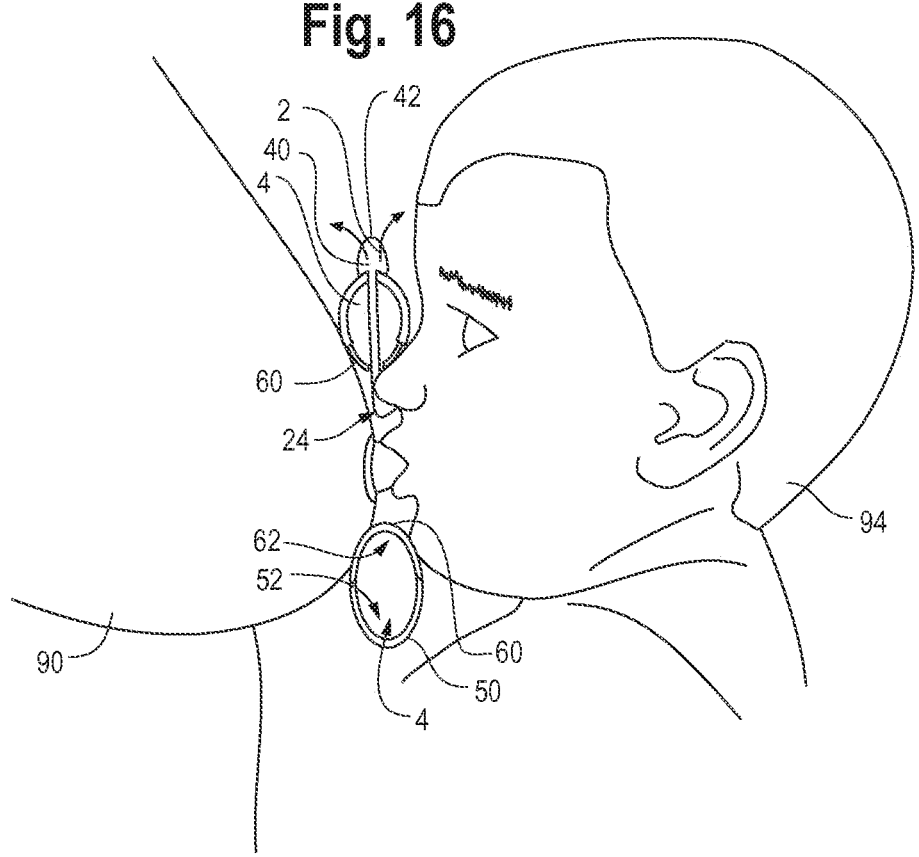
FIG. 16 is a side cross-sectional view of a user and provider with a delivery device disposed therebetween.

As shown in FIG. 15, the inner ring-like housing component 160 includes a gasket or wall 162 extending from an opposite provider side of the housing 4, but with the central space 8 being maintained as a through opening to allow access to a soother device such as a bottle 164. The gasket is shaped to engage and seal with a bottle filled for example with a fluid, such as milk or formula.

Figure 14:
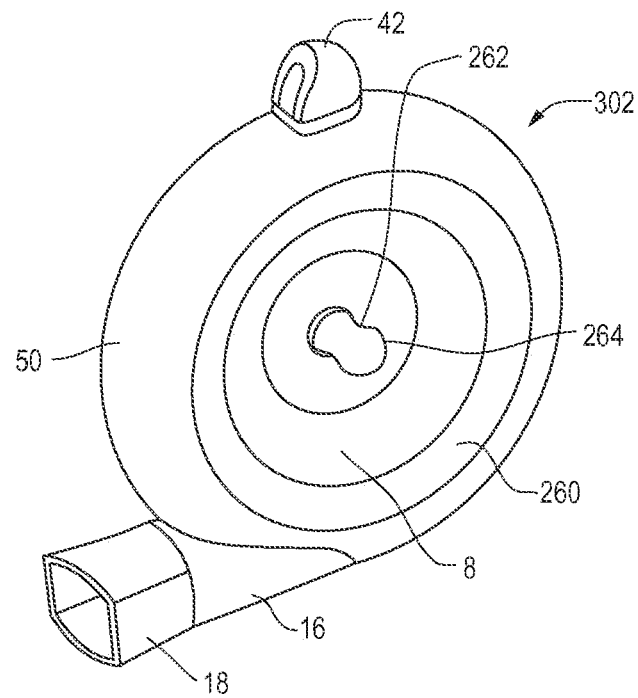
FIG. 14 is a perspective view of another alternative embodiment of a delivery device.

Referring to FIGS. 14 and 13, the central open space 8 is closed off on the provider side of the device with a wall 264, such that the central opening 8 is no longer a through opening. Rather, a soother device 262, configured as a nipple, extends from the wall 264 toward the user side where it may be accessed by the user 94.

It should be understood that in various embodiments, the various configurations of the inner ring-like housing 60, 160, 260, 360, 460 may be combined to provide a great number of different configurations suitable for various users, caregivers and situations. For example, the nasal mask 480 or the user gasket 380 may be combined with the wall 264 and soother device 262 or the bottle engaging gasket 162. One possible kit combination is shown in FIG. 3, wherein the caregiver is provided with three user soother interface options 60, 160, 260, including a breast feeding interface 60, a bottle interface 160 and a pacifier interface 260. Each of those interfaces, however, may be further configured with a nasal mask 480 or user gasket 380.

Referring to FIGS. 18-24, various alternative delivery devices are shown as including a holding chamber 700. The holding chamber may have various antistatic properties as disclosed above. As shown in FIGS. 18-21, the holding chamber has an input end 702 configured to mate with a delivery device 98, such as a pressurized metered dose inhaler. The holding chamber further includes an output end 704 configured with a baffle 712 and a one-way inhalation valve 714 in one embodiment. The output end may further include an annular flange 708 shaped to engage and support a user interface. The holding chamber may be configured with a visual indicator 706 that provides visual indicia when the user is exhaling and/or inhaling. Various suitable holding chambers are disclosed in U.S. Pat. Nos. 6,336,453, 7,360,537, 6,904,908, the entire disclosures of which are hereby incorporated herein by reference.

As shown in FIGS. 18-21, the user interface is configured as a nasal mask 600 having a flexible sealing edge 602, formed by a curved lip of the mask. The mask may be made of soft seal silicone. The sealing edge forms a generally triangular shaped opening 604, with curved sides. The opening has a curvilinear bottom edge 608, and curvilinear side edges 610 extending from the bottom edge and meeting at an apex 612. The user's nose fits in the opening 604, with the nostrils extending past the bottom edge into a cavity 614 formed in the mask. The apex 612 fits over the top of the patient's nose. The mask 600 includes an annular mounting flange 620 shaped and configured to receive the end portion 708 of the holding chamber 700 or other substance delivery device.

Figure 22:
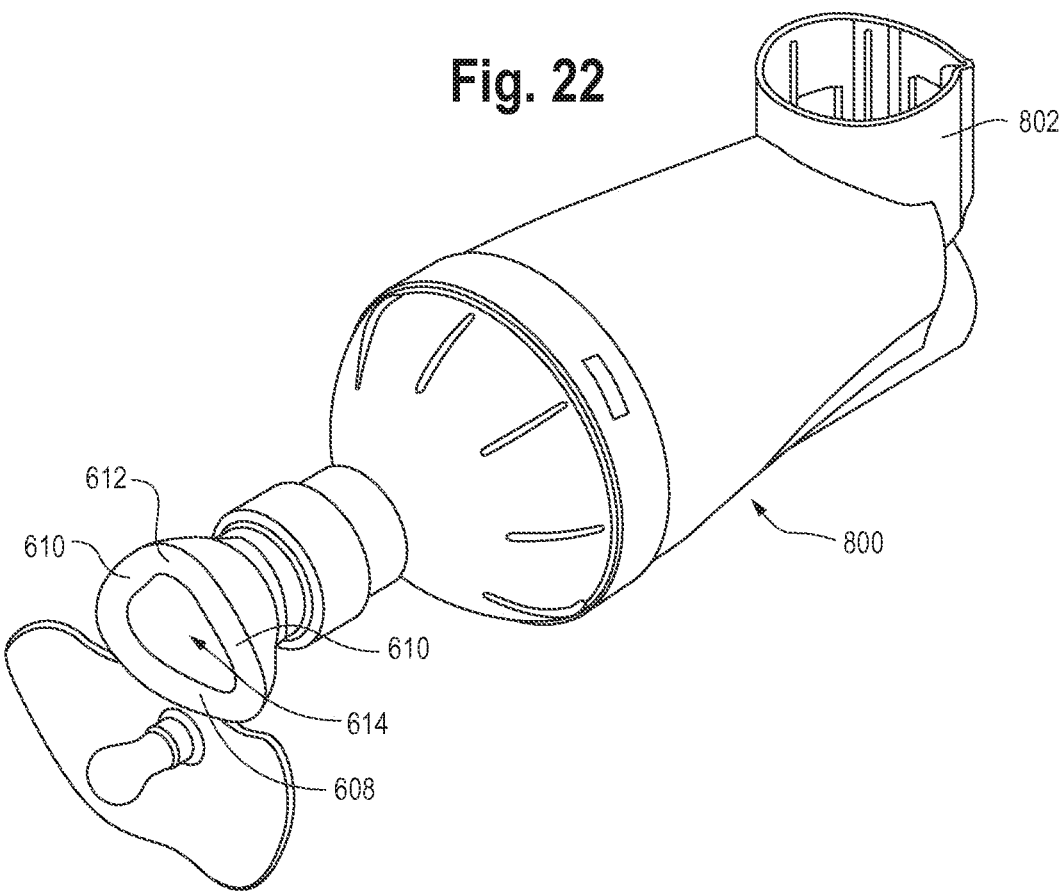
FIG. 22 is a perspective view of an alternative embodiment of a delivery device.
Figure 23:
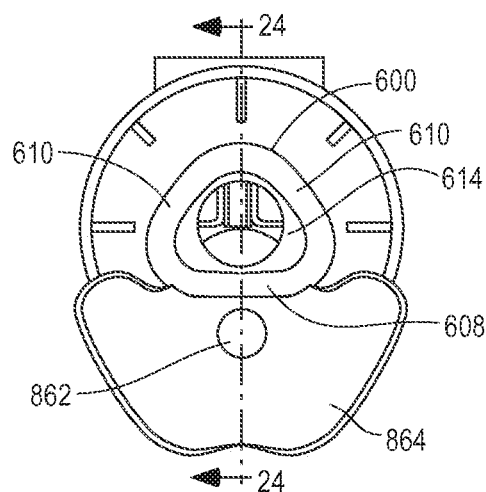
FIG. 23 is an end view of the delivery device shown in FIG. 22.
Figure 24:
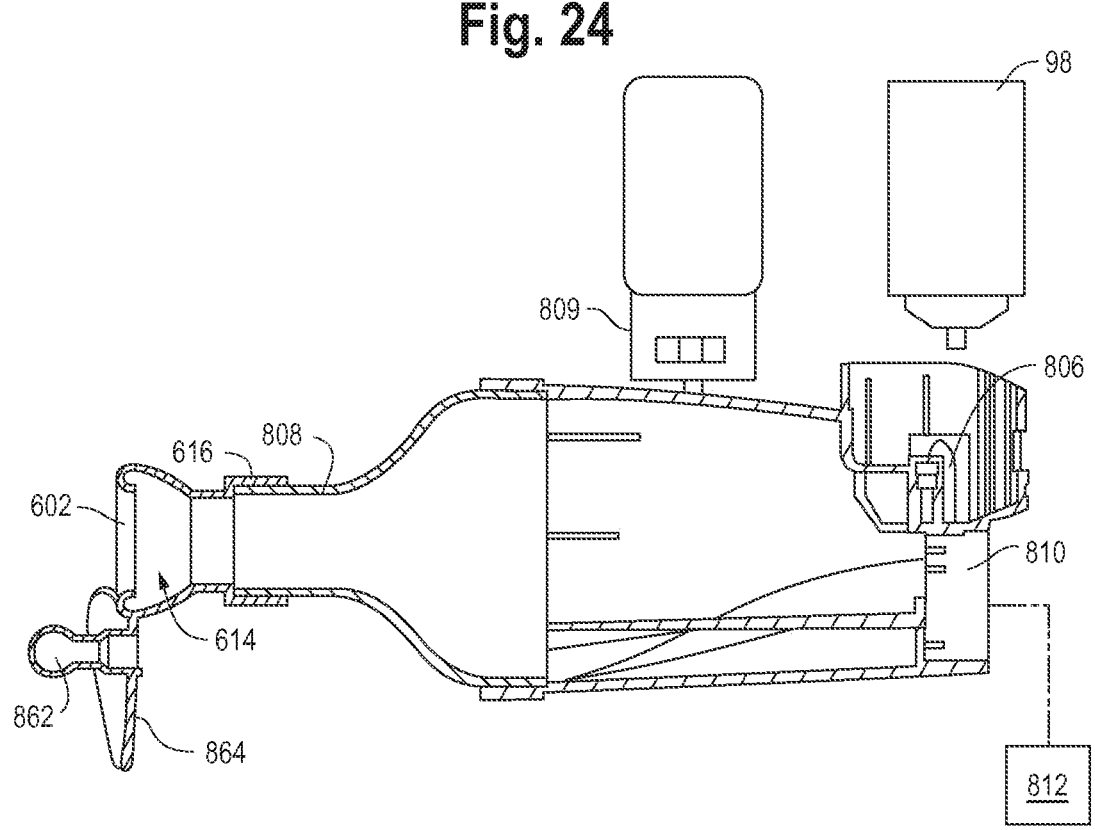
FIG. 24 is a cross-sectional view of the delivery device taken along line 24-24 of FIG. 23.

As shown in the embodiment of FIGS. 22-24, an alternative embodiment of a holding chamber 800 has a receptacle 802 for receiving the delivery device 98, which may be configured with a dose counter 804 in one embodiment. An actuator 806 actuates the dose counter when the delivery device is actuated. The holding chamber has an output end 808, which may further include an annular flange shaped to engage and support a user interface, such as the mask shown in FIGS. 18-21. The holding chamber may further include an input end 810 that is suitable for connection to a ventilator circuit 812 or other oxygen supply. Such holding chambers are further described and disclosed in U.S. Publication No. 2010/0101570 and U.S. Pat. No. 8,151,794, the entire disclosures of which are hereby incorporated herein by reference.

In this embodiment, the mask 600 further includes an integral soother device 862, or nipple, with a shield, or mouth guard 864, surrounding the soother device 362 and extends outwardly and downwardly therefrom. The shield or mouth guard has a contoured shaped suitable for mating with the chin and mouth of the user. The soother device 862 is connected to the bottom edge portion 608.

In operation, and referring to FIGS. 10-12 and 16, the housing 4 is positioned with a caregiver's breast 90 and nipple extending into the central open space 8 from a provider side of the housing. The inner ring-like housing component 60 seals against the breast 90 as shown in FIG. 12. The face of the user 94, including the nasal passageways 196 and the mouth 194, is then introduced to the central open space from the user side of the housing 4, with a mouth 194 of the user 94 latching onto the nipple of the breast 90, which functions as an oral soother device. The inner ring-like housing component 60, whether configured with a mask 480 or not, is sealed against the face of the user. If provided with a nasal mask 480, the device is positioned such that the nasal mask 480 overlies the nasal passageways 196 of the user. In alternative embodiments, other soother devices, such as a bottle nipple 164, or a pacifier nipple 262, are introduced to the user 94, who will latch onto such devices for oral soothing. When situated in these various configurations, the user may breath normally through their nose and nasal passageways 196, with air being inhaled from the input port 16 as the inhalation valve 26 opens, through the interior cavity or chamber 4 and through the delivery port 24 to the central open space 8. During exhalation, the air passes back through the delivery port 24 and through the exhalation port 40. During inhalation, the one-way exhalation valve 46 is closed, while during exhalation, the one-way inhalation valve 26 is closed, thereby creating a back-pressure and forcing the exhaled gases out through the exhalation port 40. The caregiver, whether the provider soothing the user, or a third party observer, may monitor the exhalation valve 46, and in particular the movement thereof, to confirm the patient is exhaling. Movement of the exhalation valve 46 also provides information about the quality of the seal between the breast 90 or bottle 164 and the inner ring-like housing component 60, 160 and between the user's face and the other side of the inner ring-like housing component. If the exhalation valve 46, or flow indicator, is not moving properly, the caregiver may reposition one of the breast 90, bottle 164 or user 94 to achieve better seals on both the provider and user sides of the housing 4.

Referring to the operation of the nasal mask of FIGS. 18-24, the mask 600 is placed over the nose of the infant, with the nostrils disposed in the cavity 614. The caregiver may monitor the visual flow indicator 706 to ensure a proper seal of the mask against the face of the infant. In the embodiment of FIGS. 22-24, the soother 862 may be placed in the mouth of the infant to provide comfort to the infant when the mask is placed over the nostrils.

Once a proper breathing cycle is achieved, a delivery device 98, secured to the input port 16, or receptacle, may be actuated to introduce an aerosolized medicament into the interior cavity through the input port 16. For example, the container 22 of a MDI may be reciprocally moved relative to an actuator boot 96 so as to release a metered dose of aerosolized medicament through a mouthpiece 20 coupled to the input port 16. The medicament is drawn from the interior chamber 4 through the delivery port 24 and into the central opening 8 or nasal mask 480, wherein the aerosolized medicament is inhaled by the user. The device may be actuated one or more times as needed and prescribed. The medicament or other inhalable substance, such as oxygen and/or an aromatic substance in vapor form, may be administered by a metered dose inhaler or nebulizer, and may be positioned in a ventilator circuit, or other system providing an oxygen supply 812.

Aerosolized medication that may be administered using the delivery device 98 include, without limitation, corticosteroids, such as beclamethasone, budesonide, flunisolide, cilcesonide, and fluticasone, and bronchodilators, such as albuterol, proventil, levalbuterol, salmeterol and pirbuterol.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A delivery device comprising:
  a holding chamber having an input end and an output end comprising a one-way inhalation valve;
  a nasal mask coupled to said output end, said nasal mask comprising an interior surface defining a cavity shaped to receive a user's nose without surrounding the user's mouth, an outermost exterior surface exposed to an ambient environment, a flexible bottom edge portion, and a pair of flexible side portions, said side portions extending upwardly from said bottom edge portion and connecting at an apex; and
  a soothing device coupled to and extending downwardly from said nasal mask, wherein said soothing device is disposed outside of said cavity and is exposed to the ambient environment, wherein said soothing device comprises a nipple and a shield portion surrounding said nipple, wherein said shield portion extends above said bottom edge portion.

2. The delivery device of claim 1 further comprising a substance dispenser coupled to said input end.

3. The delivery device of claim 2 wherein said substance dispenser comprises an oxygen supply.

4. The delivery device of claim 2 wherein said substance dispenser dispenses an aromatic substance in vapor form.

5. The delivery device of claim 2 wherein said substance dispenser supplies a corticosteroid in aerosol form.

6. The delivery device of claim 2 wherein said substance dispenser supplies a bronchodilator in aerosol form.

7. The delivery device of claim 1 wherein said bottom edge portion and said side portions are each curved and define a triangular shaped opening with curved sides.

8. The delivery device of claim 7 wherein the bottom edge portion and the side portions are defined by an inwardly curved lip.

9. The delivery device of claim 8 wherein said lip terminates at a free edge disposed in said cavity.

10. A delivery device comprising:
  a nasal mask comprising an interior surface defining a cavity shaped to receive a user's nose without surrounding the user's mouth, an exterior surface exposed to an ambient environment, a flexible bottom edge portion, and a pair of flexible side portions, said side portions extending upwardly from said bottom edge portion with said bottom edge portion and said side portions defining a continuous sealing edge forming a triangular shaped opening, wherein said sealing edge is defined by an inwardly curved lip terminating at a free edge disposed in said cavity;
  a holding chamber having an input end and an output end, wherein said nasal mask is coupled to said output end;
  a substance dispenser coupled to said input end of said holding chamber; and
  a soothing device extending downwardly from said bottom edge portion, wherein said soothing device is disposed outside of said cavity and is exposed to the ambient environment, wherein said soothing device is disposed outside of said cavity and is exposed to the ambient environment, wherein said soothing device comprises a nipple and a shield portion surrounding said nipple, wherein said shield portion extends above said bottom edge portion.

11. A method of delivering an inhalable substance comprising:
  positioning a nose of a user in a cavity of a nasal mask;
  positioning the mouth of the user outside of the cavity;
  disposing a flexible bottom edge portion of the mask against an upper lip of the user and a pair of flexible side portions against the face of the user with an apex connecting said bottom edge portion and said side portions fitting over a top of the user's nose, wherein the user's mouth is exposed to the ambient environment;

flowing an inhalable medicament substance from a holding chamber having an output end coupled to an input port of said mask;
introducing said inhalable medicament substance into said cavity through said input port of said mask; and
inhaling through said nose in said central opening and thereby drawing said inhalable medicament substance from said cavity; and
soothing said user by positioning a nipple of a soothing device extending downwardly from said nasal mask in said mouth of said user, and positioning a shield portion of said soothing device against a face of said user, wherein said shield portion extends above said bottom edge portion.

12. The method of claim 11 wherein said bottom edge portion and said side portions defining a continuous sealing edge forming a triangular shaped opening, wherein said sealing edge is defined by an inwardly curved lip terminating at a free edge disposed in said cavity and wherein said disposing a flexible bottom edge portion of the mask against said upper lip of the user and said pair of flexible side portions against the face of the user comprises pressing said sealing edge against the user's skin.

13. The delivery device of claim 2 wherein said substance dispenser comprises a metered dose inhaler disposed in an actuator boot having a mouthpiece, wherein said mouthpiece is disposed in said input end of said holding chamber.

14. The delivery device of claim 10 wherein said output end of said holding chamber comprises a one-way inhalation valve.

15. The delivery device of claim 14 wherein said substance dispenser comprises a metered dose inhaler disposed in an actuator boot having a mouthpiece, wherein said mouthpiece is disposed in said input end of said holding chamber.

16. The method of claim 11 wherein introducing said inhalable medicament substance into said cavity comprises flowing said inhalable medicament substance through a one-way inhalation valve located at said output end of said holding chamber.

17. The method of claim 16 further comprising flowing said inhalable medicament substance into said holding chamber from a metered dose inhaler disposed in an actuator boot having a mouthpiece, wherein said mouthpiece is disposed in an input end of said holding chamber.

18. A delivery device comprising:
a holding chamber having an input end and an output end comprising a one-way inhalation valve;
a nasal mask coupled to said output end, said nasal mask comprising an interior surface defining a cavity shaped to receive a user's nose without surrounding the user's mouth, an outermost exterior surface exposed to an ambient environment, a flexible bottom edge portion, and a pair of flexible side portions, said side portions extending upwardly from said bottom edge portion and connecting at an apex; and
a soothing device coupled to and extending downwardly from said nasal mask, wherein said soothing device is disposed outside of said cavity and is exposed to the ambient environment, wherein said soothing device comprises a nipple and a shield portion surrounding said nipple, wherein said nipple and said shield portion are integrally formed with the mask as a one-piece unit.

19. The delivery device of claim 1 wherein said shield portion has an upper edge defining a first width, a lower edge defining a second width less than said first width, and opposite side edges, wherein said side edges extend downwardly and inwardly from said upper edge to said lower edge.

20. The delivery device of claim 10 wherein said nipple and said shield portion are integrally formed with the mask as a one-piece unit.

21. The delivery device of claim 10 wherein said shield portion has an upper edge defining a first width, a lower edge defining a second width less than said first width, and opposite side edges, wherein said side edges extend downwardly and inwardly from said upper edge to said lower edge.

22. The method of claim 11 wherein said nipple and said shield portion are integrally formed with the mask as a one-piece unit.

23. The method of claim 11 wherein said shield portion has an upper edge defining a first width, a lower edge defining a second width less than said first width, and opposite side edges, wherein said side edges extend downwardly and inwardly from said upper edge to said lower edge.

* * * * *